United States Patent [19]
Nees et al.

[11] Patent Number: 6,070,459
[45] Date of Patent: Jun. 6, 2000

[54] METHOD FOR DETERMINING THE ADHESION OF MATERIAL LAYERS ON CERAMIC ELEMENTS

[75] Inventors: Siegfried Nees, Neckarwestheim; Harald Neumann, Vaihingen; Frank Stanglmeier, Moeglingen, all of Germany

[73] Assignee: Robert Bosch GmbH, Stuttgart, Germany

[21] Appl. No.: 09/040,102

[22] Filed: Mar. 17, 1998

[30] Foreign Application Priority Data

Mar. 19, 1997 [DE] Germany .......................... 197 11 378

[51] Int. Cl.$^7$ ...................................................... G01J 4/02
[52] U.S. Cl. ............................................................. 73/150 R
[58] Field of Search .................................. 73/866, 866.5, 73/150 R, 150 A; 374/57

[56] References Cited

U.S. PATENT DOCUMENTS

| | | | |
|---|---|---|---|
| 3,293,912 | 12/1966 | Kochaney | 73/150 R |
| 4,559,824 | 12/1985 | Soma et al. | 374/57 |
| 4,742,111 | 5/1988 | Chi . | |
| 4,763,529 | 8/1988 | Leonard et al. | 73/865.6 |
| 5,310,575 | 5/1994 | Friese et al. . | |
| 5,529,677 | 6/1996 | Schneider et al. . | |

FOREIGN PATENT DOCUMENTS

| 0125435 | 9/1980 | Japan | 73/150 A |
|---|---|---|---|

*Primary Examiner*—Robert Raevis
*Attorney, Agent, or Firm*—Kenyon & Kenyon

[57] ABSTRACT

A method for determining the adhesion of material layers of any composition on sintered ceramic elements, in particular of material layers on sensor elements for determining gas constituents in gas mixtures. The coated ceramic elements are immersed in an immersion bath consisting of a protic acid, and then subjected to a shock-type heat treatment. Adhesion is then assessed.

12 Claims, No Drawings

METHOD FOR DETERMINING THE ADHESION OF MATERIAL LAYERS ON CERAMIC ELEMENTS

FIELD OF THE INVENTION

The present invention relates to a method for determining the adhesion of material layers and layer systems on sintered ceramic elements, and in particular to a method for determining the adhesion of material layers on the ceramic of electrochemical sensors for determining gas constituents in gases.

BACKGROUND INFORMATION

It is generally known to use electrochemical sensors, often also referred to as lambda probes, to determine, for example, the oxygen content of exhaust gases, in particular of exhaust gases of internal combustion engines. Two principal variants of these exist. They are the "finger" probe, as described, for example, in U.S. Pat. No. 5,310,575; and as the second embodiment the "plate" probe, as described, for example, in U.S. Pat. No. 5,529,677. All the known sensors of this kind are based on the principle of the oxygen concentration chain, with an ion-conducting solid electrolyte. They contain as the probe body, for example in the case of the "finger" probe, a tube, closed at one end and made of an ionically conducting material, for example yttrium oxide-stabilized zirconium dioxide (YSZ), on the outer surface of which are located, facing the exhaust gas, a conductive path and a measurement electrode which can consist, for example, of platinum cement. In the case of the "plate" probe, the ceramic of the rod- or plate-shaped solid electrolyte consists of the same material, and here again conductive paths and a measurement electrode, which can also consist, for example, of platinum cement, are arranged on the ceramic on the surface facing the exhaust gas.

The conductive path and the measurement electrode layer or layers are very thin in these sensors, and although they generally bear additional ceramic cover layers and/or protective layers, they are nevertheless subject, after extended use, to corrosive attack by some of the exhaust gas constituents, e.g. soot and compounds of lead, phosphorus, nitrogen, and sulfur. In addition, the conductive paths and the measurement electrode layers tend, under unfavorable conditions, to detach from the ceramic element.

Until now, no satisfactory method had been proposed for determining the adhesion of such material layers, i.e. of the electrodes and the conductive path layers and any cover layers that might be present, on such ceramic elements, so as thereby to monitor production in qualitative terms.

SUMMARY OF THE INVENTION

The method according to the present invention has the advantage that the adhesion of material layers applied onto ceramic layers can be tested, in a uncomplicated and cost-effective manner, by arranging simple process steps in succession. First the coated ceramic elements are introduced into an immersion bath, and are subsequently exposed to a temperature of at least 700° C., such that the adhesion of the coating can be assessed by checking for detachment of the conductive path and also of the cover layers and protective layers. It is thereby possible in very simple fashion, during the production of, for example, lambda probes, to optimize the production process by means of a simple method.

It has been found that particularly high efficiency for the method can be achieved if the immersion bath consists of an acid bath.

Advantageously, concentrated protic acids are used in the immersion bath, selected in particular from the group HCl, $H_3PO_4$, $H_3PO_2$, $H_2SO_4$, $H_2SO_3$, $HNO_3$. By means of these acids, the chemical stress resulting from exhaust gas constituents can be simulated in the immersion bath in very simple and surprisingly efficient fashion, since the acid anions, in conjunction with a high proton concentration, imitate the effect of gaseous compounds of the corresponding elements, for example nitrogen oxides, phosphines, phosphides, sulfates, sulfites, etc.

In a preferred embodiment, the immersion bath consists of at least two baths, at least one bath being an acid bath consisting of a protic acid which simulates the exhaust gas situation at the probe body, and a second bath consisting of water being used, so that any residues of the protic acid, or reaction products thereof, that might adhere externally can be rinsed off.

In a particularly preferred embodiment, the residence time of the coated ceramic elements in the immersion bath is at least one hour, so that even with an extended residence time, continuous operation of, for example, a probe body of a so-called lambda probe can thereby be simulated.

In an advantageous embodiment, the ceramic elements are subjected, after the immersion bath, to a temperature treatment with a particularly short temperature rise time, so that a shock temperature difference is achieved, so that any detachment of the conductive path or of the cover or insulation layers takes place quickly. The temperature gradient should therefore be no less than 10° C./sec. In a particularly preferred embodiment, the temperature during the temperature treatment is 700 to 1000° C., so that the conditions in an exhaust gas, in particular of internal combustion engines, can thereby be simulated particularly well.

In a further advantageous embodiment, the coated ceramic elements are subjected, after the immersion bath, to a continuous temperature treatment so that the latter are slowly heated from ambient temperature to 700 to 1000° C. This makes it possible, in a very simple fashion, to simulate the process of heating-up a catalytic converter, and consequently the lambda probe as well, when an internal combustion engine is started.

In a further preferred embodiment, there can be used as the ceramic elements all of the sensor elements for the determination of gas constituents in gas mixtures which have a coating of any layer sequence of any materials, for example a sequence of metal compounds and/or glass compounds and/or ceramic compounds and/or cement compounds and/or electrically and ionically conductive compounds. It is thus possible with this method, in a very simple fashion, to simulate the stress on such sensor elements for any gases, for example NO, $SO_2$, and to check the adhesion of the layers on the sensor elements.

DETAILED DESCRIPTION

A lambda finger probe, described for example in U.S. Pat. No. 5,310,575, having a conductive path made of platinum cement and a protective slip layer made of porous ceramic, is introduced by means of a holder into a bath of concentrated sulfuric acid for a period of 24 hours. After removal from the bath, the lambda probe ceramic treated in this fashion is immersed in water, thus removing any acid residues that may be adhering externally. After this rinse, the lambda probe ceramic is heat-treated in a furnace by means of shock heating at a gas temperature of 900 to 1000° C. In the subsequent visual inspection, the nature, location, and size of the detached layers on the ceramics are assessed, regarding both detachment of the conductive path and detachment of the cover layer. In the event of poor adhesion, both the protective layer and the conductive paths detach at least locally. It is also disadvantageous, however, if only the cover layer, consisting of slip, is detached, thus exposing the conductive path to the corrosive attack of exhaust gases in internal combustion engines, so that its function is also severely impaired. Adhesion of the layers is particularly poor if, in addition to the slip layer, the conductive path also partially detaches, and the bare ceramic probe body made of YSZ emerges. Proper operation of the sensor element can then no longer be guaranteed. This method therefore not only tests the mechanical strength of the applied layer system, but simultaneously also takes into account the strength under chemical and thermal stress, such as is present during continuous operation in the exhaust gases of an internal combustion engine.

What is claimed is:

1. A method for determining an adhesion of a coating on a ceramic element, comprising the steps of:
   introducing the coated ceramic element into an immersion bath;
   after removing the coated ceramic element from the immersion bath, exposing the coated ceramic element to a heat treatment; and
   after removing the coated ceramic element from the heat treatment, assessing a damage to the coating.

2. The method according to claim 1, wherein the immersion bath consists of an acid bath.

3. The method according to claim 2, wherein the acid bath includes at least one protic acid selected from the group consisting of: HCl, $H_3PO_4$, $H_3PO_2$, $H_2SO_4$, $H_2SO_3$, and $HNO_3$.

4. The method according to claim 1, wherein the immersion bath consists of at least two baths, a first one of the at least two baths being an acid bath.

5. The method according to claim 4, wherein the acid bath includes at least one protic acid selected from the group consisting of: HCl, $H_3PO_4$, $H_3PO_2$, $H_2SO_4$, $H_2SO_3$, and $HNO_3$.

6. The method according to claim 5, wherein a second one of the at least two baths is a water bath.

7. The method according to claim 1, wherein a residence time of the coated ceramic element in the immersion bath is at least one hour.

8. The method according to claim 7, wherein a temperature during the heat treatment is between 700° and 1000° C.

9. The method according to claim 1, wherein a temperature gradient of the heat treatment is greater than 10° C./sec.

10. The method according to claim 1, wherein a temperature during the heat treatment is slowly raised to between 700° and 1000° C.

11. The method according to claim 1, wherein the ceramic element is part of a sensor element.

12. The method according to claim 1, wherein the ceramic element includes at least one of the following: metal compounds, glass compounds, ceramic compounds, cement compounds, and electrically and ionically conductive compounds.

* * * * *

UNITED STATES PATENT AND TRADEMARK OFFICE
CERTIFICATE OF CORRECTION

PATENT NO. : 6,070,459
DATED : June 6, 2000
INVENTOR(S) : Siegfried Nees, et. al.

It is certified that error appears in the above-identified patent and that said Letters Patent is hereby corrected as shown below:

Column 1, line 34, change "... CEMENT..." to --... CERMET... --.

Column 2, line 52, change "... CEMENT..." to --... CERMET... --.

Column 4, line 27, change "... CEMENT..." to --... CERMET... --.

Signed and Sealed this

First Day of May, 2001

Attest:

NICHOLAS P. GODICI

Attesting Officer       Acting Director of the United States Patent and Trademark Office